(12) United States Patent
Wheeler (10) Patent No.: US 11,755,902 B2
(45) Date of Patent: Sep. 12, 2023

(54) CO-ADAPTATION FOR LEARNING AND CONTROL OF DEVICES

(71) Applicant: THE CHARLES STARK DRAPER LABORATORY, INC., Cambridge, MA (US)

(72) Inventor: Jesse J. Wheeler, Revere, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1047 days.

(21) Appl. No.: 16/427,287

(22) Filed: May 30, 2019

(65) Prior Publication Data

US 2019/0370650 A1 Dec. 5, 2019

Related U.S. Application Data

(60) Provisional application No. 62/679,533, filed on Jun. 1, 2018.

(51) Int. Cl.
*G06N 3/08* (2023.01)
*G06F 3/01* (2006.01)
(Continued)

(52) U.S. Cl.
CPC ............... *G06N 3/08* (2013.01); *G06F 3/013* (2013.01); *G06F 3/015* (2013.01); *G06N 3/061* (2013.01); *G06N 5/02* (2013.01)

(58) Field of Classification Search
CPC . G06N 3/08; G06N 3/061; G06N 5/02; G06F 3/015; G06F 3/016; G06F 3/017; G06F 3/011; G06F 3/012; G06F 3/013
(Continued)

(56) References Cited

U.S. PATENT DOCUMENTS 9,717,440 B2   8/2017  Abdelghani et al.
10,766,137 B1 * 9/2020  Porter ...................... B25J 9/161
(Continued)

FOREIGN PATENT DOCUMENTS

WO   2006073915 A2   7/2006
WO   2014025765 A2   2/2014

OTHER PUBLICATIONS

Richard S. Sutton; Andrew G. Barto, "Eligibility Traces," in Reinforcement Learning: An Introduction , MIT Press, 1998, pp. 163-192. (Year: 1998).*

(Continued)

*Primary Examiner* — Jason D Mitchell
(74) *Attorney, Agent, or Firm* — Brooks Kushman P.C.

(57) ABSTRACT

A method of operating a biological interface is disclosed. The method may include obtaining an input physiological or neural signal from a subject, acquiring an input set of values from the input signal, obtaining a predictive signal from the subject or the environment, acquiring a predictive set of values from the predictive signal, training a decoder function in response to data from the predictive set of values, performing at least one calculation on the input set of values using the decoder function to produce an output set of values, and operating a device with the output set of values. A biological interface system is also disclosed. The biological interface system may contain an input signal sensor, an input signal processor, a predictive signal processor, a memory device storing data, and a system processor coupled to the memory device and configured to execute a decoder function.

29 Claims, 3 Drawing Sheets

(51) Int. Cl.
*G06N 3/06* (2006.01)
*G06N 5/02* (2023.01)

(58) Field of Classification Search
USPC .......................................................... 706/25
See application file for complete search history.

(56) References Cited

U.S. PATENT DOCUMENTS

| | | | | |
|---|---|---|---|---|
| 2003/0093129 | A1* | 5/2003 | Nicolelis | G06F 3/016 607/45 |
| 2007/0016265 | A1* | 1/2007 | Davoodi | G09B 19/003 607/48 |
| 2010/0092267 | A1* | 4/2010 | Najdovski | G06F 3/016 414/7 |
| 2010/0137734 | A1 | 6/2010 | Digiovanna et al. | |
| 2010/0331976 | A1 | 12/2010 | Pesaran et al. | |
| 2014/0364703 | A1* | 12/2014 | Kim | A61B 5/6824 600/301 |
| 2016/0195928 | A1* | 7/2016 | Wagner | G06F 1/163 345/156 |
| 2018/0032082 | A1* | 2/2018 | Shalev-Shwartz | G01C 21/3602 |
| 2018/0067558 | A1* | 3/2018 | Eagleman | G10L 15/16 |
| 2018/0102030 | A1* | 4/2018 | Khoshkava | H02K 35/00 |
| 2018/0260700 | A1* | 9/2018 | Nagaraja | G06N 5/043 |
| 2019/0087973 | A1* | 3/2019 | Kaehler | G06F 3/013 |
| 2019/0121522 | A1* | 4/2019 | Davis | G02B 27/017 |

OTHER PUBLICATIONS

Communication under Article 94(3) EPC from the European Patent Office in European Patent Application No. 19177665.7 dated Aug. 21, 2020.
Lotte F. et al., "A Review of Classification Algorithms for EEG Based Brain-Computer Interfaces: A 10 Year Update", Journal of Neural Engineering, Institute of Physics Publishing, (2018) vol. 15, No. 3, pp. 1-28.
Extended European Search Report of corresponding EP Application No. 19177665.7-1216 dated Sep. 23, 2019.
J. J. Wheeler, "Brain-Computer Interfaces using Electrocorticography and Surface Stimulation," Washington University in St Louis, 2018.
J. J. Wheeler, J. J. Williams, J. C. Williams, W. Wang, and D. W. Moran, "Multi-dimensional control using and ECoG-based brain-computer interface with coadaptive decoder," presented at the Society for Neuroscience Conference, 2012.

* cited by examiner

CO-ADAPTATION FOR LEARNING AND CONTROL OF DEVICES

CROSS-REFERENCE TO RELATED APPLICATIONS

This application claims priority under 35 U.S.C. § 119(e) to U.S. Provisional Application No. 62/679,533 titled "CO-ADAPTATION FOR LEARNING AND CONTROL OF DEVICES," filed Jun. 1, 2018, which is incorporated herein by reference in its entirety for all purposes.

FIELD OF TECHNOLOGY

Aspects and embodiments disclosed herein relate to systems and methods for neural interface. In particular, the systems and methods disclosed herein relate to user intent prediction using a brain-computer interface.

SUMMARY

In accordance with an aspect, there is provided a method of operating a biological interface. The method may comprise obtaining an input signal from a subject, acquiring an input set of values from the input signal, obtaining a predictive signal, acquiring a predictive set of values from the predictive signal, training a decoder function in response to data from the predictive set of values, performing at least one calculation on the input set of values using the decoder function to produce an output set of values, and operating a device with the output set of values. The input signal may comprise a neural or physiological signal. The predictive signal may comprise at least one subject predictive signal or at least one environmental predictive signal.

The predictive signal may comprise at least one of the subject predictive signal and at least one of the environmental predictive signal.

In some embodiments, acquiring the predictive set of values from the predictive signal may comprise training a predictive decoder function in response to data from the at least one of the subject predictive signal and data from the at least one of the environmental predictive signal. Acquiring the predictive set of values from the predictive signal may comprise performing at least one calculation with the predictive decoder function to produce the predictive set of values.

The subject predictive signal may comprise a physiological signal. The physiological signal may comprise at least one of an eye tracking signal, voice signal, movement signal, cardiac signal, skin conductance signal, neural signal, and muscular signal.

The environmental predictive signal may comprise at least one of an orientation signal, location signal, surroundings signal, temporal signal, sound signal, visual signal, verbal command, and visual command.

The environmental predictive signal may be associated with a software log of actions.

In accordance with certain embodiments, the method may comprise performing the at least one calculation on the input set of values and on the predictive set of values using the decoder function to produce the output set of values.

In some embodiments, the method may further comprise re-training the decoder function in response to data from a feedback set of values. The feedback set of values may be associated with a feedback signal. The feedback signal may be obtained by the operation of the device.

The feedback signal may be associated with a discrepancy between the predictive signal and an actual signal.

The actual signal may comprise at least one of a movement signal and a selection signal.

The method may further comprise presenting the actual signal to a user in the form of at least one of visual movement of the device, visual movement of a cursor on a display of the device, visual representation of control, auditory representation of control, vibrotactile stimulation, and electrical stimulation.

In some embodiments, re-training the decoder function may comprise obtaining a weight value associated with the feedback signal. The method may further comprise re-training training the decoder function in accordance with the weight value.

The weight value may be determined responsive to historical feedback signals.

The method may further comprise presenting the predictive signal to a user in the form of at least one of visual movement of the device, visual movement of a cursor on a display of the device, visual representation of control, auditory representation of control, vibrotactile stimulation, and electrical stimulation.

In some embodiments, the method may comprise obtaining a training set of values from a historical set of input signals and a historical set of predictive signals. The method may further comprise re-training the decoder function in response to data from the training set of values.

The method may further comprise updating decoder parameters with a weighted combination of data from a new training set of values and a past training set of values.

In some embodiments, a weight of the weighted combination may be determined by at least one of uncertainty and performance of the decoder.

The method may further comprise re-training the decoder at predetermined intervals comprising at least one of fixed intervals, adaptive intervals determined by performance of the device, and periodic intervals determined by a user.

The method may further comprise re-training the decoder responsive to at least one of targets for control of the device and targets selected from the environment.

The method may further comprise presenting the target to the user through a visual display, augmented reality display, or virtual reality display.

In certain embodiments, the predictive signal may comprise an eye tracking signal and an environmental signal. The method may comprise operating an electronic device with the output set of values to make a selection from a menu.

In certain embodiments, the predictive signal may comprise an eye tracking signal and an environmental signal. The method may comprise operating a mechanical device with the output set of values to actuate motion of the mechanical device.

In accordance with another aspect, there is provided a biological interface system. The biological interface system may comprise an input signal sensor, an input signal processor, a predictive signal processor, a memory device storing data from at least one of the input signal sensor, the input signal processor, and the predictive signal processor, and a system processor coupled to the memory device. The input signal sensor may be configured to collect a neural or physiological signal from a subject. The input signal processor may be configured to generate an input set of values associated with the neural or physiological signal. The predictive signal processor may be configured to generate a predictive set of values associated with a predictive signal.

The system processor may be configured to execute a decoder function. The decoder function may be configured to program the processor to receive the data from the predictive signal processor and provide the predictive set of values to the decoder function to train the decoder function, receive the data from the input signal processor and provide the input set of values to the decoder function, and perform at least one calculation on the input set of values using the decoder function to generate an output set of values. The biological system interface may be connectable to a device to be operated based on the output set of values.

The input signal sensor may comprise at least one of a microphone, a motion sensor, a temperature sensor, a light sensor, a camera, a chemical sensor, a galvanic skin response sensor, a heart rate monitor, a blood pressure monitor, an external electrode grid, an intracranial electrode grid, an intraneural electrode grid, and an intramuscular electrode grid.

In some embodiments, the system may further comprise a predictive signal subsystem configured to collect the predictive signal from at least one of the subject and an environment of the system. The memory device may store data from the predictive signal subsystem.

In certain embodiments, the predictive signal subsystem may comprise at least one subject signal sensor and at least one environmental signal sensor.

The predictive signal subsystem may comprise at least one of a microphone, a motion sensor, a temperature sensor, a light sensor, a camera, a chemical sensor, a galvanic skin response sensor, a heart rate monitor, a blood pressure monitor, an external electrode grid, an intracranial electrode grid, an intraneural electrode grid, an intramuscular electrode grid, a global positioning system, a clock, an orientation sensor, and a computer processor configured to obtain the predictive signal from an interconnected network.

In some embodiments, the device may comprise at least one of a mechanical device and an electronic device.

The system may further comprise a feedback sensor. The feedback sensor may be configured to collect an actual signal from the device. The system may further comprise a feedback signal processor. The feedback signal processor may be configured to generate a feedback set of values from the actual signal.

In certain embodiments, the decoder function may further be configured to program the system processor to receive the data from the feedback signal processor and provide the feedback set of values to the decoder function to re-train the decoder function.

The system may comprise a display device. The display device may be configured to display at least one of the predictive signal and an actual signal.

The device may comprise a display device. The display device may be configured to display a target.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Biologically controlled devices can be controlled by neural interfaces, for example, brain-computer interfaces (BCI), and physiological signals, for example, eye motion and hand motion signals. Input features from the subject may be monitored and converted into control signals. Neural interfaces can include invasive, non-invasive, or partially invasive interfaces. Similarly, physiological signals may be monitored via invasive, non-invasive, or partially invasive interfaces. For BCI, the signals may be neural signals recorded from the brain, for example, with electrodes. The neural signals may be obtained from electrodes implanted within the brain, near to and around the brain, or from the outer surface of the head. The neural signals may be obtained from an epidural or cranial electrocorticography (ECoG). For wearable devices, the signals may be electromyographic (EMG) signals or inertial measurement unit (IMU) signals. The EMG and IMU signals may be obtained from a sensor attached to a limb of the user. The features extracted from the signals may include time-domain amplitudes and wavelets, spectral power and phase from different frequency bands, and correlation and coherence between signals, optionally recorded from multiple electrodes or sensors. Signals from more than one type of feature may be combined to create a more complete input value.

Neural signals (which may include neural signals from the brain, neural signals from the central and peripheral nervous systems, or electrical stimulation through muscles) and weak EMG (below thresholds for movement) may be employed for controlling systems without the direct use of a person's limbs and hands (for example, a BCI). Some example applications of these human-machine (or human-computer) interfaces include neuroprosthetics for amputees or paralyzed individuals, and hands-free augmented reality and virtual reality headsets. In these applications, neural signals may be monitored on the individual and translated into control signals that may move motorized prosthetic joints, move cursors in software, or execute actions like clicking a software button, or typing a message. In these applications, the human volitionally controls the system by modulating their neural signals in order to achieve their goal. For example, in neuroprosthetics, the subject thinks about movement in order to generate appropriate neural signals that can be used by the human-machine system to move a prosthetic limb. In other applications, the subject's control may be coordinated with additional subject's control or autonomous agents. While the disclosure describes various embodiments specific to prosthetic limbs, it should be understood that the embodiments described herein are not limited to prosthetic limbs, but are applicable to other devices that translate neural or physiological signals into device performance.

In accordance with certain embodiments, the input signal may be a physiological signal or a neural signal. The input signal may be provided by the subject to obtain an output set of values or control values. For instance, the input signal may be provided to move a device or cursor. The input signal may be provided to actuate control of a mechanical device or make a selection on a menu. In a biological interface system, the input signal may be measured, recorded, or otherwise obtained by an input sensor. The input signal may be converted to an input set of values for processing, for example, by a processor. Physiological signals which can be employed as the input signal include, for example, at least one of an eye tracking signal, voice signal, movement signal, cardiac signal, skin conductance signal, neural signal, and muscular signal. The input signal may be voluntary or involuntary. Exemplary voluntary input signals include, for example, eye motion, voice commands, hand gestures, muscle contraction, and others. Involuntary input signals may include, for example, pupillometry, heart rate, sweating, involuntary muscle contractions, and others. In certain embodiments, the physiological signal may be unperceivable to a user without the aid of a sensor device. For instance, pupillometry signals may be are unperceivable to the naked eye of an observer.

Eye tracking signals may generally include signals for point of gaze or motion of the eye relative to the head. Such signals include eye rotation, eye fixations, eye saccades, eye micro-saccades, and pupillometry. In exemplary embodiments, eye fixations may be used to determine subject's intent. Pupillometry may be used to determine the subject's cognitive load and attention.

Voice signals may generally include vocal articulations, such as voice commands, and other vocal sounds, such as those generated by sighing, laughing, crying, screaming, grunting, and others.

Movement signals may generally include motion signals from limbs or body parts, for example, arms, hands, fingers, legs, eyes, and others.

Cardiac signals may generally include heart rate signals, for example, resting heart rate, maximum heart rate, pulse, and $VO_2$ max.

Skin conductance signals may generally include electrodermal activity measurements, for example, skin conductance, resistance, potential, impedance, and admittance. In general, skin conductance signals may be associated with activity of the sweat glands. Skin conductance may be measured on any external topical surface of the subject.

Neural signals may generally include electrochemical signals produced and/or propagated by a nervous system tissue.

Muscular signals may generally include a determination of the presence or absence of a muscle contraction, and optionally the anatomical location of contracted or relaxed muscle tissue. Muscular signals may additionally include the length and/or tension of a muscle contraction.

The disclosure is not limited to the physiological signals described herein. Other physiological signals may be considered, including, for example, blood pressure, composition of a bodily fluid, respiratory rate, composition of a bodily gas or exhaled air, and others.

Physiological signals may be employed for controlling distant objects or converting gestures to text or auditory messages. The physiological signals may be measured, recorded, or otherwise obtained by a physiological sensor. The physiological sensor may be wearable or otherwise connectable to a target anatomical feature of the subject. The physiological sensor may be positioned to collect a physiological signal from the subject.

The physiological sensor may be employed as the input sensor. The input sensor may include, for example, one or more of a microphone, a motion sensor, a temperature sensor, a light sensor, a camera, a chemical sensor, a galvanic skin response sensor, a heart rate monitor, blood pressure monitor, an external electrode grid, an intracranial electrode grid, an intraneural electrode grid, and an intramuscular electrode grid. Other input sensors for obtaining physiological signals are within the scope of the disclosure.

One example of a device is a communication device that can translate gestures or body movements into auditory commands. Yet other applications are within the scope of the disclosure. Decoder functions may be employed to receive and translate the input signal into an output signal, for example, a desired control signal. This may be accomplished by first applying signal processing techniques to extract useful information (or features) from the recorded input signals, for example, physiological signals. For example, in multi-unit neural recordings, spiking rate may be used as a feature, which is the rate at which a neuron fires action potentials. In other examples, like electromyography, local field potential, electrocorticography, and electroencephalography, spectral power estimation methods may be applied to estimate the modulation of power in specific frequency bands, and the power modulation may be used as features. In one exemplary embodiment, an electrode array may have Y number of electrodes, each with Z number of frequency bands (channels). Such an electrode array may be configured to measure, record, or obtain Y×Z features. In yet other examples, body gestures or eye movements may be used as a feature. Processors may be employed to drive the biologically controlled device according to the input signal. The device to be controlled may be hardware or software.

Feature sets are often of higher dimension than the number of control signals desired, and may contain similar or redundant information. In order to reduce the dimensionality, techniques like Independent Component Analysis and Principle Component Analysis may be used to transform the features into a lower-dimensionality feature set. Features may be fed into to the decoder that combines the features (linearly or nonlinearly) and outputs control signals. Examples of decoders include Kalman Filters, Gaussian Filters, Optimal Linear Estimators, Population Vector Algorithms, and varieties of Neural Networks. In some cases, the feature extraction and decoding are combined together in a single step. Using multi-layer neural networks as an example, upper layers may expand input signals into features that are represented in intermediate layers and then condense the features into output control signals in the lower layers.

Predictive signals may be used to train the decoder function. A combination of predictors obtained from the subject and the environment of the subject may be used to predict intent of the subject, for example, at the time when the subject provides the input signal. The combination of signals may be used to accurately and rapidly determine intent, such that error in actual control of the device is minimized. The methods may comprise obtaining a predictive signal and processing the predictive signal to acquire a predictive set of values, for example, with a processor.

Intent may be inferred from the subject or from the environment of the subject. The predictive signal may include a subject predictive signal and an environment predictive signal. In particular embodiments, the predictive signal may include both a subject predictive signal and an environmental predictive signal. The one or more subject predictive signals and environment predictive signals may be combined with a predictive decoder function. For instance, the method may include training the predictive decoder function with data from a plurality of predictive signals (for example, historical predictive and/or input signals stored on a memory device) and performing a calculation on a predictive signal to produce a predictive set of values. The data may be weighted, as described in more detail below. In certain embodiments, the predictive signal may be stored and provided by a memory device and system processor. For instance, the predictive signal may be obtained from a software log of historical data or a software log of actions.

The subject predictive signal may generally comprise a signal generated by the subject. The subject predictive signal may be a physiological signal, as described above. The subject predictive signal may be the same or different from the input signal. The subject predictive signal may be a voluntary or involuntary physiological signal. In certain embodiments, the subject predictive signal may be an involuntary physiological signal. For example, the subject predictive signal may comprise an involuntary signal while the input signal may comprise a voluntary signal.

The subject predictive signal may be measured, recorded, or otherwise obtained by a subject signal sensor. The subject signal sensor may be or comprise any physiological signal sensor described above. The subject signal sensor may be the same or different from the input signal sensor.

The environmental predictive signal may generally comprise a signal obtained from the environment of the subject. In a biological interface system, the environmental signal may be measured, recorded, or otherwise obtained by an environmental signal sensor. Environmental signals which can be employed as the predictive signal include, for example, at least one of an orientation signal, location signal, surroundings signal, temporal signal, sound signal, visual signal, verbal command, and visual command. The environmental signals may be perceivable or unperceivable to the subject. For example, certain sounds are unperceivable to the naked ear.

Orientation signals may generally include orientation data of the subject or an external subject or object of interest relating to positioning on a three-dimensional plane. The orientation data may include, for example, orientation relative to a point of interest. In certain embodiments, the point of interest may be a surface, for example, the ground, a floor, a ceiling, or a wall.

Location signals may generally include geolocation data relating to a latitude, longitude, and/or altitude positioning of the subject or an external subject or object of interest. The geolocation data may be considered as location on a map or within a building or room.

Surroundings signals may generally include all other signals relating to the surroundings of the subject, for example, architecture, weather, external temperature, and others.

Temporal signals may generally include temporal data comprising, for example, time elapsed from a first event to the present or to a second event, time of day, day of week, day of month, day of year, season of year, and others.

Sound signals may generally include auditory signals, for example, conversational sounds, traffic sounds, warnings, alarms, and all other environmental sounds.

Visual signals may generally include visible signals, for example, relating to the environment or situation of the subject. In certain embodiments, the visual signals may include signs, for example, traffic signs, instructional signs, and other visible cues. In an exemplary embodiment, a visible cue may be a rope generally indicating that a line or queue is to be formed adjacent to the rope. In another exemplary embodiment, a visible cue may be a menu at a restaurant generally indicating that a selection from the menu is appropriate. In yet another exemplary embodiment, a visible cue may be a watch or clock generally indicating an approximation of the time of day. Other visual cues are within the scope of the disclosure.

Verbal commands and visual commands may generally include voluntary verbal or visual signals executed by the subject or another. Verbal commands may include vocal articulations or vocal sounds, for example, providing instructions or feedback. Visual commands may include movement, gestures, or other visual indications to draw attention in a particular direction.

Any one or more of the predictive signals, for example, environmental signals may be obtained by a computer processor configured to obtain the signal from an interconnected network. In particular embodiments, the system may be connected to a network and configured to receive environmental signals. The environmental signals may include, for example, weather information, temporal information, geolocation information, and others.

The disclosure is not limited to the environmental signals described herein. Other environmental signals may be considered, including, for example, composition or population of a room or location, speed or identity of a passing object, and others.

The environmental predictive signals may be measured, recorded, or otherwise obtained by an environmental sensor. The input sensor may include, for example, one or more of a microphone, a motion sensor, a temperature sensor, a light sensor, a camera, a chemical sensor, a global positioning system, a clock, an orientation sensor. Other environmental sensors for obtaining environmental predictive signals are within the scope of the disclosure.

Decoder functions may be employed to receive and translate the predictive signal into an output signal, for example, a desired control signal. In accordance with certain embodiments, the decoder function may receive and translate the input signal and the predictive signal to produce the output signal. In particular, the method may comprise performing at least one calculation with the input set of values and/or the predictive set of values with the trained decoder function to produce the output set of values. The output set of values may be used to actuate control of the device.

Thus, a biological interface system as described herein may include an input signal sensor, an input signal processor, and a predictive signal processor. The predictive signal processor may be connectable to an interconnected network to receive the predictive signal. The biological interface system may further include a predictive signal sensor, for example, in embodiments where the predictive signal is not obtained from an interconnected network. The biological interface system may further include a memory device electrically connected to and configured to store data from one or more of the sensors and processors. The memory device may be any memory device known to one of ordinary skill in the art, and may be electrically connectable to a sensor or processor via any means known to one of ordinary skill in the art.

The biological interface system may additionally include a system processor coupled to the memory device. The system processor may be any system processor known to one of ordinary skill in the art. The system processor may be coupled to the memory device by any means known to one of ordinary skill in the art. In particular, the system processor may be configured to execute the decoder function to obtain an output set of values. The output set of values may be employed to operate a device. Thus, the biological interface system may be connectable to a device to be operated based on the calculations made by the decoder function.

The decoder function may be configured to program the system processor. In general, the decoder function may be configured to program the system processor to receive data relating to the predictive signal and provide a predictive set of values to train the decoder function. The decoder function may further be configured to program the system processor to receive data relating to the input signal and provide the input set of values to the decoder function. The decoder function may be configured to program the system processor to perform at least one calculation on the input set of values using the decoder function to generate an output set of values, which may be employed to operate the device. Thus, the decoder function may be configured to enable the system processor to operate the device more accurately and with less lag time than conventional biological interface systems.

The decoder may be derived or trained based upon mathematical relationships between the input signals, predictive signals, and the desired output signals. For regression models, this may be accomplished by assuming that control signals can be derived from inputs via a linear transformation that can be represented as a matrix multiplication. The Optimal Linear Estimator (OLE) is an example of a linear transformation method based upon a regression model. Here, it is assumed that there is a training dataset consisting of desired control signals, K, and features, F, that may be mapped onto K. For this example, K is a matrix of T time points by D dimensions to be controlled. F is a matrix of T time points by N number of features. The desired decoder, C, is the matrix that can be multiplied by F in order to achieve K. C is determined by the following:

Training data sets for the OLE typically consist of two aligned time series data sets organized as matrices of T time samples, N numbers of normalized features, and D desired kinematic control signals:

$$F:[T \times N] = \begin{bmatrix} f_{t_1}^{n_1} & f_{t_1}^{n_2} & \cdots & f_{t_1}^{N} \\ f_{t_2}^{n_1} & f_{t_2}^{n_2} & \cdots & f_{t_2}^{N} \\ \vdots & \vdots & \ddots & \vdots \\ f_{t_T}^{n_1} & f_{t_T}^{n_2} & \cdots & f_{T}^{N} \end{bmatrix} \quad (1)$$

$$K:[T \times D] = \begin{bmatrix} k_{t_1}^{d_1} & k_{t_1}^{d_2} & \cdots & k_{t_1}^{D} \\ k_{t_2}^{d_1} & k_{t_2}^{d_2} & \cdots & k_{t_2}^{D} \\ \vdots & \vdots & \ddots & \vdots \\ k_{T}^{d_1} & k_{T}^{d_2} & \cdots & k_{T}^{D} \end{bmatrix} \quad (2)$$

where F and K refer to features and desired kinematic control signals, respectively. The OLE assumes that K can be constructed by matrix multiplication of F by a matrix of regression coefficients C which represent the weighted contributions of each feature:

$$C:[N \times D] = \begin{bmatrix} c_{n_1}^{d_1} & c_{n_1}^{d_2} & \cdots & c_{n_1}^{D} \\ c_{n_2}^{d_1} & c_{n_2}^{d_2} & \cdots & c_{n_2}^{D} \\ \vdots & \vdots & \ddots & \vdots \\ c_{N}^{d_1} & c_{N}^{d_2} & \cdots & c_{N}^{D} \end{bmatrix} \quad (3)$$

$$K = FC \quad (4)$$

Therefore, C is estimated by the following:

$$C = F^+ K = ((F^T F)^{-1} F^T) K \quad (5)$$

where $F^+$ is the pseudoinverse of F. Note that in order to include a constant bias term, $c_0$, in the regression models, an additional column of 1's is added to the feature matrix such that $F:[T \times N+1]$ and $C:[N+1 \times D]$.

Other models may be used for the decoder. Generally, a mathematical model is constructed from known predictive signals and desired control signals. In laboratory settings, the desired control signals can be easily derived through well-defined tasks and instructions for the user. For example, the user may be instructed to try to move a cursor to a desired target on a computer screen. The user may be instructed to grasp a cup with a prosthetic hand. In these examples, the desired user intent is known and the decoder function can be constructed to link the input signals to the desired action.

Error-correction may be needed when a task is performed incorrectly. In open-loop models, the decoder may not be trained by user feedback. A large data set may be required to avoid overfitting. Furthermore, this approach may require generalizing across subjects. Thus, in systems that employ open-loop functions, the subject is often faced with learning and correcting errors internally, for example, by intentionally overshooting a target by a learned error margin. In the laboratory setting, determining error-correction may be simplified because the task to be completed is known. In an unsupervised setting, where the subject is not instructed to complete a specific task, error-correction generally becomes more complex.

In practice, it has been difficult to train and re-train a decoder function in an unsupervised setting, for example, outside a laboratory setting. Without instructions for the user, it has been difficult to derive desired control signals and provide accurate feedback. The systems and methods described herein may be employed to accurately and rapidly train and re-train a decoder function in an unsupervised setting, using predictive signals to infer user intent and feedback signals obtained from operation of the device.

Feedback from the user may be incorporated during training of the decoder. Feedback data can be used to create a closed-loop system that can account for multiple data sets, non-stationary signals, and subject-uniqueness. Feedback can be generated by direct sensing. The system may include a feedback sensor configured to collect an actual signal from operation of the device. The feedback sensor may be a physiological or environmental sensor, as previously described. The actual signal may be converted to a feedback set of values by a feedback signal processor. For example, data may be gathered while a subject watches the desired task being completed. Data may be gathered while the subject attempts to complete the desired task. In some embodiments, the subject can watch a prosthetic or cursor move to a desired target. Feedback can be generated by indirect sensing. For example, data may be gathered while auditory sounds are modulated with finger flexion. In some embodiments, the decoder may be continuously trained with feedback data. Once trained, the decoder may be static or further corrected by using predictions of desired control taken during use.

The methods disclosed herein may further comprise re-training the decoder function in response to data from the feedback signal obtained by operation of the device. In general, the feedback signal may be associated with a discrepancy between the predictive signal and the actual signal. For instance, the feedback signal may comprise a degree of discrepancy between the subject's predicted intent and the actual operation of the device.

The actual signal, associated with the actual operation of the device, may comprise at least one of a movement signal and a selection signal. The movement signal may include movement of a mechanical device and movement of a cursor on an electronic device. The selection signal may comprise selection of an object to interact with or of an option on a menu. In accordance with certain embodiments, the actual signal may be presented to a user in the form of at least one of visual movement of the device, visual movement of a cursor on a display of the device, visual representation of control, auditory representation of control, vibrotactile stimulation, and electrical stimulation. Feedback from the actual operation of the device may be presented to the user as stimulation to modulate medical therapy, physiological function, cognition, or psychiatric state.

As disclosed herein, a user may be the subject or another individual. For instance, the user may be an operator. The operator may be a medical provider or a system operator.

In certain embodiments, the input signal and/or the predictive signal may be presented to a user. The signals may be presented for approval by the user. The input signal and/or predictive signal may be presented to the user in the form of at least one of visual movement of the device, visual movement of a cursor on a display of the device, visual representation of control, auditory representation of control, vibrotactile stimulation, and electrical stimulation. Feedback from the input signal and/or predictive signal of the device may be presented to the user as stimulation to modulate medical therapy, physiological function, cognition, or psychiatric state.

The decoder function may be further configured to program the system processor to receive feedback signal data and re-train the decoder function with the feedback set of values. Co-adaptation may incorporate feedback or error-correction to iteratively improve the decoder while the subject is attempting control. During periods of system control by a subject, a slightly inaccurate decoder may miss the desired user's intent. However, as long as the user's true intent is known, the error can be corrected by iteratively re-training and fine-tuning the decoder. Outside of controlled settings, where the user is unsupervised, it is generally more difficult to determine their intent, and as such, may be more difficult to train and correct the decoder. In such systems, other information can be used to make estimates of the user's intent. The predicted user intent can be used as a proxy to correct and improve the decoder using co-adaptation. The systems and methods disclosed herein may use predictive signals to infer user intent and train the decoder function accordingly.

The decoder function may be re-trained by feedback data in response to a weight value attributed to the feedback data. The weighted value may prevent an outlying actual response from completely re-training the decoder function. In particular embodiments, the weight value may be determined responsive to historical input, predictive, environmental, or feedback signals. For instance, previous feedback signals may be distinguishable from the current actual signal, generally indicating that the current actual signal is an outlier in a complete set of feedback signals.

In some embodiments, the method may comprise obtaining a training set of values from a historical set of input signals and a historical set of predictive signals. The historical data may be stored on a memory device and accessed by the system processor. Data from the training set of values may be used to re-train the decoder function in addition to or instead of re-training with the feedback values.

In certain embodiments, the decoder parameters may be updated with a weighted combination of data from a new training set of values and past training set of values. The weight attributed to each training set may be determined by at least one of uncertainty and performance of the decoder. For instance, weights may be determined by uncertainty of decoder updates, i.e. confidence or goodness-of-fit. Weights may be determined by performance of decoders in controlling the device.

In general, the decoder may be re-trained at predetermined intervals. The intervals may be fixed intervals, adaptive intervals determined by performance of the device, and/or periodic intervals determined by a user.

In exemplary embodiments, the decoder may be re-trained at fixed intervals, for example, every hour, every 6 hours, every 12 hours, or every day.

In other embodiments, performance of the device may instruct the decoder that re-training is needed. The method may comprise re-training the decoder responsive to at least one of targets for control of the device and targets selected from the environment. The target may be presented to the user through a visual display, augmented reality display, or virtual reality display. For example, if discrepancy between the predictive signal and the actual signal is greater than a predetermined threshold or outside tolerance of a predetermined target value, the feedback signal may re-train the decoder. In an exemplary embodiment for movement of the device, the threshold or target value may be a predetermined distance from the predictive target. In an exemplary embodiment for selection, the threshold or target value may be a predetermined number of correct selections, for example, 90%, 80%, 70%, 60%, or 50% of the actual selections matching the predictive selection. Thus, the target may be a target location or selection. In general, predetermined training paradigms may include targets for device control that are presented to the user. Ad hoc training paradigms may include targets selected from the environment.

In other embodiments, the decoder may be re-trained as instructed by the user.

The biological interface system may additionally include a visual display coupled to the memory device and/or to the system processor. the visual display may be used to display one or more signal obtained by a sensor or from an interconnected network. The visual display may be configured to display a status of the biological interface system, for example, an operational status or a warning message.

The biological interface system may include an input device configured to receive instructions on operation of the system, for example, a mouse, keyboard, or touch pad. The input device may be used to select one or more sensor, processor, or program for operation of the system. The input device may be used to access stored memory data.

The biological interface system may be connectable to a power source. The power source may be an internal or external power source. The power source may be any power source known to one of ordinary skill in the art. The power source may be connectable to the biological interface system by any means known to one of ordinary skill in the art. The biological interface system may be connectable to a device to be operated based on the output set of values calculated by the decoder function. The device may be a mechanical or electronic device. In particular embodiments, the mechanical device may be, for example, a prosthetic device or robotic device. The mechanical device may employ the output set of values to actuate movement of the device or a portion of the device. In certain embodiments, the electronic device may employ the output set of values to move a cursor or make a selection from a menu. In particular, the output set of values may instruct, for example, velocity of the cursor in one dimension, two dimensions, or three dimensions. The device may comprise a display device configured to display, for example, a target, information relating to an operational status of the device, or a warning sign.

In certain exemplary embodiments, signals that can be used to predict user intent include eye tracking. By monitoring what the user is looking at and fixating on, the system can predict that the subject wants to move to the object or interact with the object in a known way. Another signal that can be used is pupillometry, which has been shown to be a good measure of cognitive load and attention. By knowing that the subject is looking at an object and has heightened awareness, the system can predict that the object being looked at is of importance and is related to the user's intent. Another example signal is behavioral monitoring. Software logging may provide a history of how the subject has behaved previously in similar contexts. The log can be used to predict the subject's next intended action. Other cognitive, behavioral, neural, and physiological predictive signals can be employed. These predictive signals can also be combined (for example by a Bayesian filter) to improve the prediction of the subject's intent. Once the subject's intent is predicted, it can be used to correct the decoder without the need for supervision. Exemplary devices that can be used to collect the predictive signal include cameras, ECoG, EMG, IMU, eye tracking, galvanic skin response, and computer hardware and software. Other devices and methods of signal sensing may be employed, as previously described.

In one example, a camera on a pair of glasses can be used to detect that a prosthetic arm is moving toward a glass. It may be assumed that the subject is attempting to grab and lift the glass. The predicted control can be used with recorded signals to create new data sets to train and correct the decoder.

Figure 1:
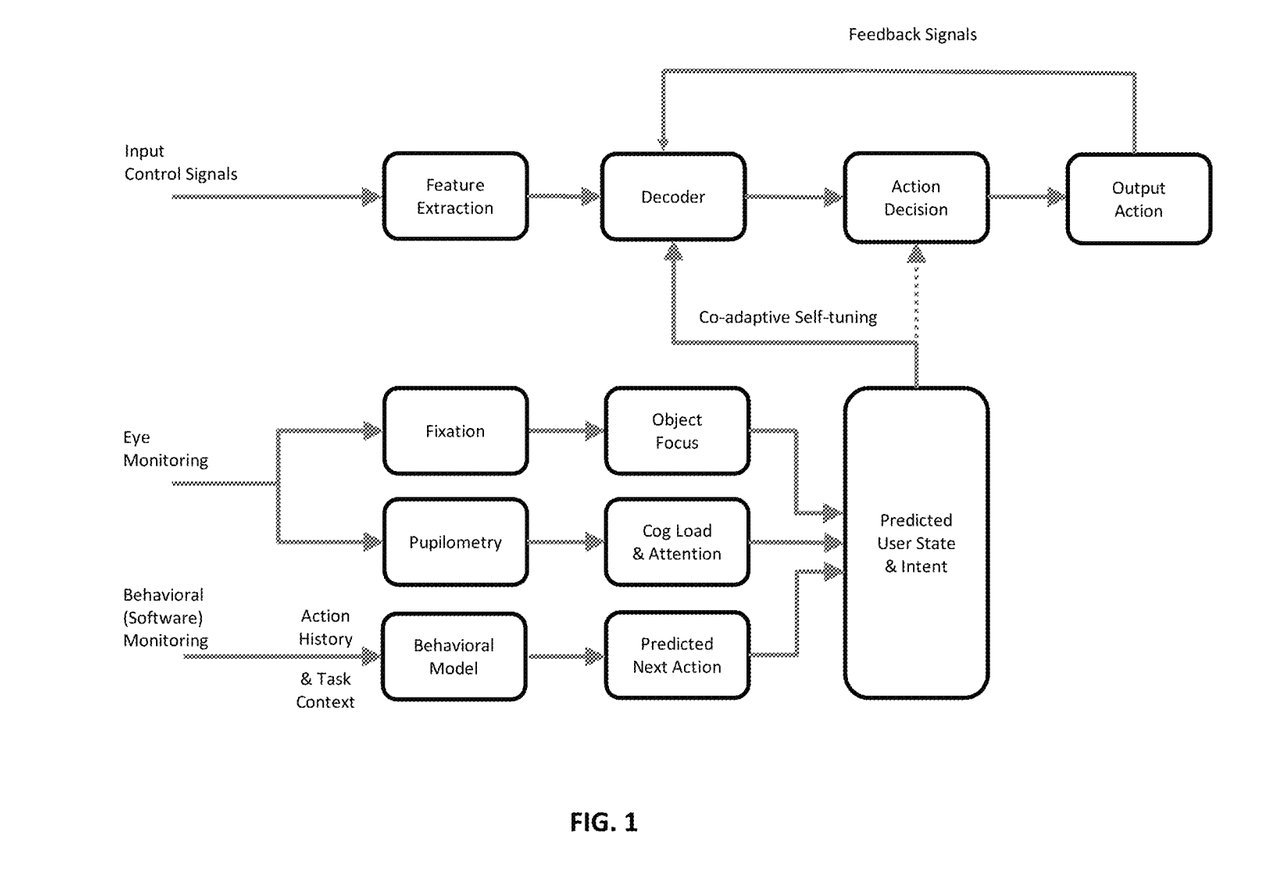
FIG. 1 is a box diagram of an exemplary method of operating a biological interface, according to one embodiment.

FIG. 1 is a box diagram of an exemplary method of operating a biological interface. In the exemplary method of FIG. 1, input control signals are processed with a decoder function after undergoing feature extraction. The method includes processing predictive signals, including eye monitoring and behavioral monitoring, to predict user state and intent. The eye monitoring signals include fixation and pupillometry. Specifically, the fixation signals provide information associated with object focus, while the pupillometry data provides information associated with user cognition and attention. The behavioral monitoring is obtained from a software log which processes action history and task context (environmental signals). The method includes processing the behavioral monitoring data to predict a user's next action. In some embodiments, the eye monitoring signals are user-specific, while the behavioral monitoring signals may be generalized for all users or a specific population of users. The method includes predicting user state and intent data to train a decoder function. The trained decoder function may be employed to process the input signals and output an action. In some embodiments, the method may include providing feedback data to further train the decoder function.

In some embodiments, co-adaptive functions may be employed to accelerate learning and interface system performance. Co-adaptation combines machine learning with subject learning such that both occur together in optimal fashion. In particular, the co-adaptive functions may improve performance by providing approximate real-time error-correction to tune a signal decoder. Such a co-adaptive function may be employed similar to how feedback is used in control theory to reduce errors and improve system performance. Additionally, co-adaptive functions may be employed to correct for non-stationarities in signals. These non-stationarities have been a challenge in conventional systems.

In some embodiments, error feedback can be used to create directed training tasks to improve control. For example, when controlling two-dimensional cursor movement on a computer screen, larger errors may be detected during movement in a first plane (e.g., left-right movement) than movement in a second plane (e.g., up-down movement). In response to these large errors between predicted control and actual control, a set of training tasks may be created to collect additional data in the second planar direction to be used to improve the decoder.

Neural networks may be desirable for their potential in providing open-loop decode accuracy, but the time required to train them is long. Faster and accurate training of a closed-loop co-adaptive function may be achieved through iterative learning techniques. In some embodiments, co-adaptive learning functions may be combined with advanced deep learning techniques to iteratively train combined convolution and recurrent neural networks and implement a precision decoder.

Multiple training sets (input signals or predictive signals) can be combined in a weighted manner when updating the decoder. Multiple decode parameter sets resulting from separate training sets may also be combined in a weighted manner. For example, new parameters can be combined with older parameters using a low pass filter. New parameters may be more highly weighted than old parameters to promote faster change. This weighting scheme can be adapted when control has been poor to accelerate correction. Alternatively, new parameters can be weighted lower than old parameters to avoid drastic changes. This weighting scheme can be adopted when decoder robustness is valued.

Multiple parameters can be combined with a Gaussian filter. Gaussian filters generally provide the ability to estimate uncertainty in the decoder output. The uncertainty can be used to modulate the co-adaptive learning rate or can be used as part of a multi-input Bayesian filter. Multiple parameters can be combined with a Bayesian filter. The Bayesian filter can optimally combine input control (for example, neural signals) with control estimates from user intent (for example, predictive signals) from other sources.

Figure 2:
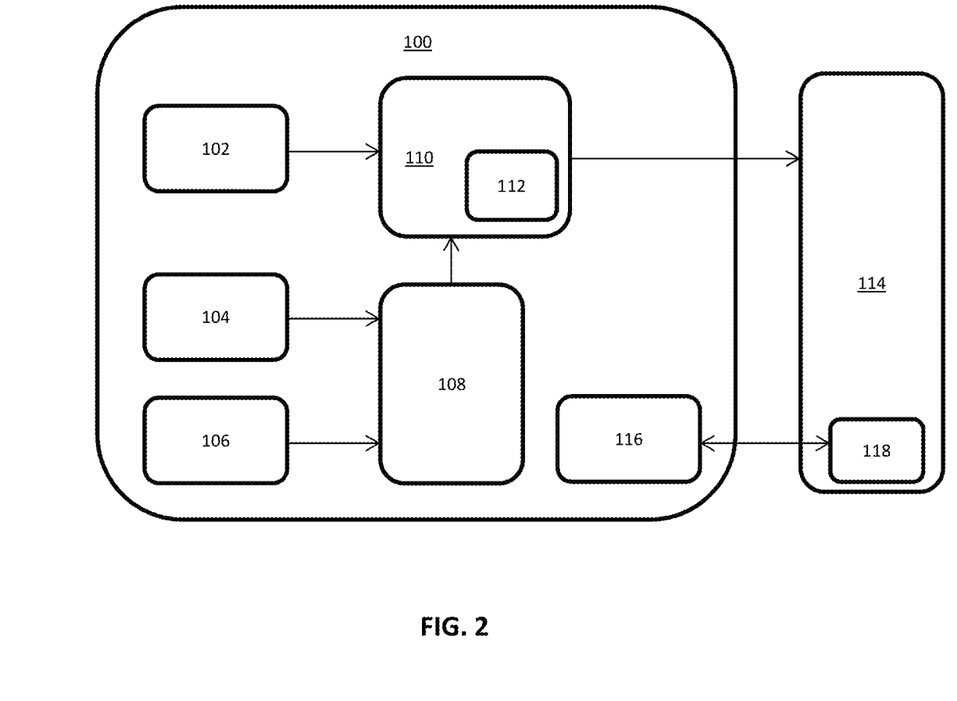
FIG. 2 is a box diagram of an exemplary biological interface system, according to one embodiment.

FIG. 2 is a box diagram of an exemplary biological interface system. The system 100 may be worn or attached to the subject. Device 102 may function as the input signal sensor. Device 102 may include, for example, micro-electrodes, ECoG, EFEG, or EEG. In the exemplary system 100 an EFEG array 102 functions as the input signal sensor. A camera 104 including an eye tracker functions as the predictive signal sensor. The system includes a predictive signal processor 108. A software program 106 that logs data based on previous actions also provides predictive signals to the predictive signal processor 108. The predictive signal processor 108 and input signal sensor are in communication with a system processor 110 including memory device 112. A controlled or biological device 114 may receive control signals from, and optionally, be operated by the system processor 110. The system 100 may include a power circuit 116, optionally in electrical communication with a battery 118 included in the device 114. The system may further include one or more signal amplifiers or drivers (not shown). The system 100 or device 114 may include one or more displays (not shown). In one exemplary embodiment, the device 114 may include a visual display that could be implemented with virtual reality or augmented reality.

Conventionally, it is difficult to achieve four degree-of-freedom (DoF) or 6 DoF control in a neural interface system. Control with 4 DoF can be achieved with invasive micro-electrode recordings using only the highest spatiotemporal resolution possible. Alternatively, control with 4 DoF can be achieved in a laboratory setting with a minimally invasive epidural ECoG. However, feature training with high accuracy, scalability, and speed is necessary to effectively improve neural interface system performance, for example, BCI performance. Using the systems and methods disclosed herein the time required to train the network may be reduced to achieve rapid closed-loop error-correction. Accordingly, control with 6 DoF can be achieved in a neural interface system beyond the laboratory setting.

Figure 3:
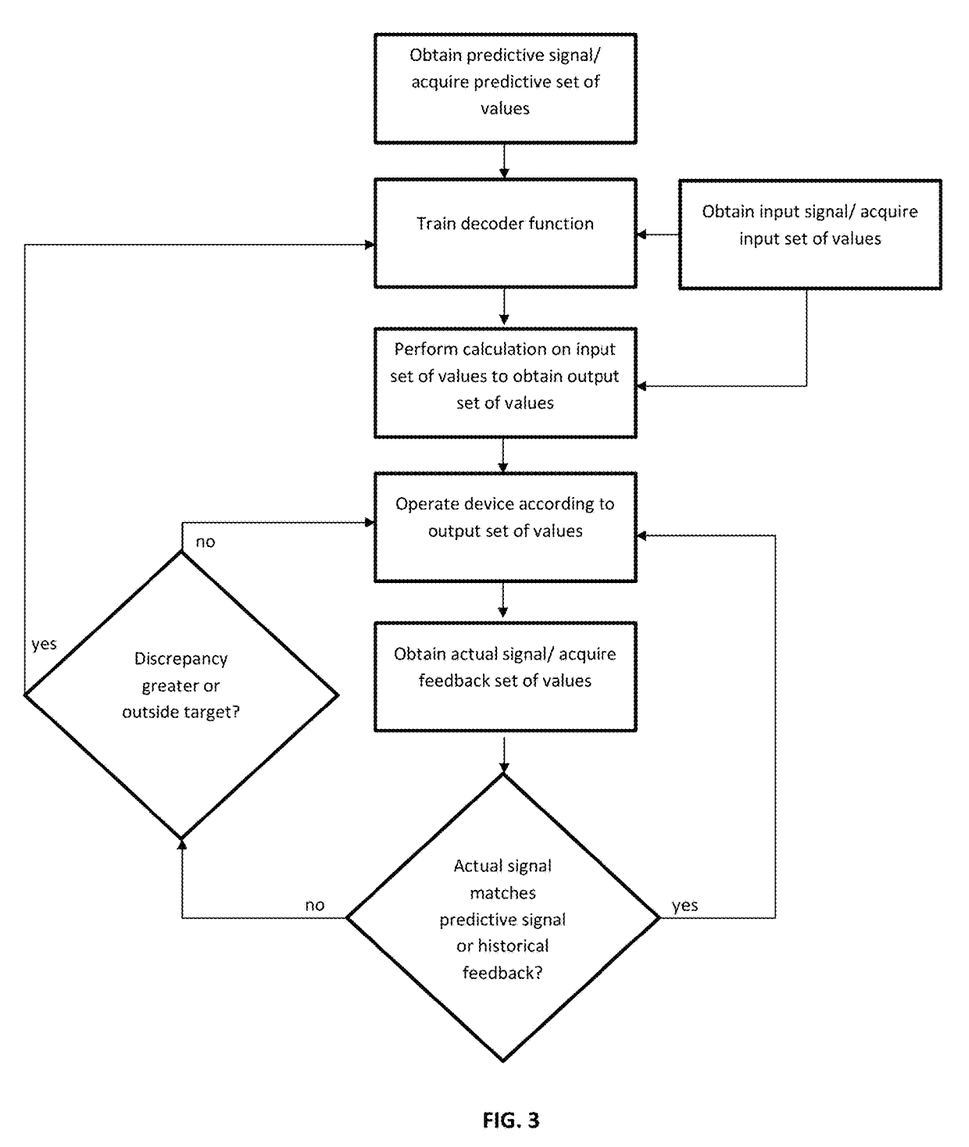
FIG. 3 is a flow diagram of an exemplary method of operating a biological interface, according to one embodiment.

FIG. 3 is a flow diagram of an exemplary method of operating a biological interface. The exemplary method may include obtaining a predictive signal and acquiring a predictive set of values. The method may include training a decoder function responsive to the predictive set of values. The method may also include obtaining an input signal and acquiring an input set of values. In certain embodiments, historical input values may be used to train or re-train the decoder function. The method may include performing a calculation on the input set of values with the decoder function to produce an output set of values. The method may include operating the device with the output set of values. The method may include obtaining an actual signal from operation of the device and acquiring a feedback set of values from the actual signal. If the actual signal matches the predictive signal or a target historical data, operation of the device may continue. If there is a discrepancy between the actual signal and the predictive signal or the target historical data, the discrepancy can be evaluated to determine whether the discrepancy is greater than a predetermined threshold target or outside tolerance of a target range. If the discrepancy is great, the decoder function may be retrained responsive to the feedback set of values, optionally in a weighted manner. If the discrepancy is within tolerance, operation of the device may continue. In the exemplary method, re-training of the decoder function may additionally be triggered in fixed intervals or as instructed by a user.

EXAMPLES

The embodiments may be further understood with reference to the following examples. The examples are intended to serve as an illustration and are not limiting.

Prophetic Example 1: BCI System with Predictive Modeling for Feedback Control and Error-Correction An exemplary BCI system is configured to integrate neural inputs and an eye-tracking system (fixation location and pupillometry). Neural signals can be used to decode motor control, cognitive load, and attention. Pupillometry signals can be used to obtain cognitive signals, which provide a good baseline biomarker for comparison with neural estimates. Eye-tracking signals can provide a method of estimating subject intent and can be used for error-correction with the co-adaptive decoder in unsupervised tasks where the subject is free to play within the BCI environment. A preliminary analysis of candidate decoding techniques includes convolution neural networks, recurrent neural networks, Kalman Filters, Gaussian filters, and optimal linear estimators. Proficiency with the BCI can be achieved in less time by using decoders that can be trained faster through iterative techniques. For example, Gaussian filters may be used as decoders because they provide an estimate of uncertainty in the decoder output.

The BCI system is operated to explore ways that decoders can be trained faster through iterative learning techniques. Gaussian filters are promising due to their ability to provide an estimate of uncertainty in the decoder output. This uncertainty can be used to modulate the co-adaptive learning rate, or can later be used as part of a multi-input Bayesian filter that optimally combines neural control with control estimates of user intent from other sources (for example, eye tracking, and behavioral monitoring).

It is believed that operation of the BCI by the methods of predictive feedback described herein will achieve more efficient training and accuracy than conventional methods. Decoding algorithms can be chosen based upon accuracy, scalability, and speed of training. Similarly, an algorithm can be down-selected based upon low accuracy, scalability, and speed of training. In addition, signal processing can be added to minimize any stimulation artifact that generally occurs in recorded neural data.

To improve error-correction for the co-adaptive decoder in unsupervised use, technology can be integrated into the BCI environment to allow logging of past behavioral data and context. This data can be used to enable predictions of the subject's intent based upon their past behavior and current situation. This additional input is combined with existing estimates of user intent to further improve the BCI performance. The BCI system can be used outside of supervisory control, which will be needed for translating BCI use to the real-world.

Accordingly, the BCI system can be used to operate a device with high accuracy and quick error-correction even when the user intent is not explicitly provided.

Prophetic Example 2: BCI System with Predictive Modeling for Feedback Control and Error-Correction for Controlling a Prosthetic Arm To control a prosthetic arm, an exemplary BCI system is provided which includes a neural sensing system, a camera system that senses the subject's view (including object identification), and an eye-tracking system (fixation location and pupillometry). Neural signals can be used to decode motor control, cognitive load, and attention. Pupillometry signals can be used to obtain cognitive signals, which provide a good baseline biomarker for comparison with neural estimates. Eye-tracking signals can provide a method of estimating subject intent and can be used for error-correction with the co-adaptive decoder in unsupervised tasks where the subject operates the BCI freely and without instruction.

Initial training may occur within a clinical setting where the decoder is trained to translate neural signals into control of a prosthetic arm. The initial training may include instructions from a user or a well-defined task in which the subject is provided commands or cues that indicate an action or goal that the subject is to achieve. Decoding techniques may include convolution neural networks, recurrent neural networks, Kalman Filters, Gaussian filters, and optimal linear estimators.

Later training can occur in an unsupervised setting, for example, away from the clinic, when the subject is using the BCI freely to interact with objects in his or her environment. Decoder training may occur even without the subject being aware of the training. Because a clinician is not present to provide instructions to the subject to initiate desired actions and goals, subject intent is estimated from other available signals, including eye tracking, pupillometry, and brain activity.

As the subject is using the BCI, the decoder automatically initiates an update. Initiation of the update may occur at regular programmed intervals, or upon detection of degraded performance. For example, the smoothness of movement trajectories or time taken to move may be recorded over time and when these metrics begin to degrade, the decoder may automatically be updated to improve performance. Alternatively, the subject may elect to update the decoder based upon a voice command or selection of a button.

During the update, the eye tracking system may monitor which objects in the subject's environment the subject is most often focused on. An algorithm may be used to determine the object of interest and de-noise spurious saccades. In one example, the subject may look at a water bottle on a table that they intend to grasp with their prosthetic arm. An estimated arm movement and hand grasp that the subject is intending to make may be determined. At each moment in time, the next predicted movement may be recorded along with the neural activity that is driving the prosthetic arm.

In some cases, the predicted action can be improved by combining information about prior actions during similar conditions. For example, a log of actions and corresponding behavioral model may be used to predict that after pouring water from a bottle into a glass, the next likely action is to pick up the glass. To improve the accuracy of movement, the movement direction may be biased toward the predicted final orientation based upon where the eyes are fixated. In this way, the direction of eye gaze may be used with the neural signals to improve control. The error between the predicted movement based upon eye-gaze and actual movement creates a feedback signal to the decoder.

The amount that the decoder is changed may be dependent upon the goodness-of-fit, or uncertainty, of the newly calculated decoder. Gaussian filters are promising due to their ability to provide an estimate of uncertainty in the decoder output. This uncertainty could be used to modulate the co-adaptive learning rate. For example, if there is a lot of uncertainty, only a small change will be made in the decoder parameters. Alternatively, if there is little uncertainty, a larger change will be made in the decoder. The amount that the decoder is updated can also be based upon the prior performance of the BCI using, for example, the metrics related to the smoothness and speed of movement trajectory. The uncertainty of the decoder can also be used as part of a multi-input Bayesian filter that optimally combines neural control with control estimates of user intent from other sources (for example, eye tracking, and behavioral monitoring) in order to improve performance.

It is believed that operation of the BCI will lead to rapid iterative training using the disclosed decoders. An algorithm can be down-selected based upon accuracy, scalability, and speed of training. In addition, signal processing can be added to minimize any stimulation artifact that generally occurs in the recorded neural data. To improve error-correction for the co-adaptive decoder in unsupervised use, technology can be integrated into the BCI environment to allow logging of past behavioral data and context. This data can be used to enable predictions of the subject's intent based upon their past behavior and current situation. This additional input is combined with existing estimates of user intent to further improve the BCI performance. The BCI system can be used outside of supervisory control, which will be needed for translating BCI use to the real-world.

Accordingly, the BCI system can be used to operate a device with high accuracy and quick error-correction even when the user intent is not explicitly provided. Such a BCI system can be used to accurately operate a prosthetic arm.

Prophetic Example 3: BCI System with Predictive Modeling for Feedback Control and Error-Correction for Controlling an Augmented Reality Headset To control an augmented reality headset, an exemplary BCI system is provided which includes a neural sensing system, electromyographic (EMG) sensing system, a camera system that senses the subject's view (including object identification), an eye-tracking system (fixation location and pupillometry), and an augmented reality headset. Neural signals and EMG can be used to decode motor control, cognitive load, and attention. Pupillometry signals can be used to obtain cognitive signals, which provide a good baseline biomarker for comparison with neural estimates. Eye-tracking signals can provide a method of estimating subject intent and can be used for error-correction with the co-adaptive decoder in unsupervised tasks where the subject operates the BCI freely and without instruction. An augmented reality headset can be used to display menu items, predicted actions, information, and highlight objects of interest within the subject's view.

Initial training may occur by following pre-defined training sessions where specific tasks/actions are presented to the subject. The subject attempts to perform the tasks/actions using their neural and EMG signals. For example, a virtual cursor may appear on the augmented reality display and the subject may be instructed to move it to a target. The target can be an object that is projected in augmented reality, or an actual object in front of the user that is illuminated by the augmented reality headset. The training session may use an algorithm to choose targets in certain directions in order to improve the distribution of targets in such a way that it will improve the accuracy of the decoder. Decoding techniques may include convolution neural networks, recurrent neural networks, Kalman Filters, Gaussian filters, and optimal linear estimators.

Later training may occur when the subject is using the BCI freely to interact with objects in their environment. Decoder training may occur even without the subject being aware of the training. In later training sessions, the subject intent is estimated from other available signals, including eye tracking, pupillometry, brain activity, and behavioral models.

As the subject is using the BCI, the decoder may automatically initiate an update. Initiation of the update may occur at regular programmed intervals, or upon detection of degraded performance. For example, the smoothness of virtual cursor movement trajectories or time taken to select a virtual menu item may be recorded over time and when these metrics begin to degrade, the decoder may automatically be updated to improve performance. Alternatively, the subject may elect to update the decoder based upon a voice command or selection of a button.

During the update, the eye tracking system may monitor which objects in the subject's augmented environment the subject is most often focused on. An algorithm may be used to determine the object of interest and de-noise spurious saccades. In one example, the subject may enter a busy sidewalk and look at the street signs. The BCI system may predict that the subject wants to navigate somewhere. An icon to initiate navigation may appear, along with other icons for common tasks, and a cursor for selecting the desired action. Once the desired navigation action is selected, the BCI system may predict that the subject wants to find lunch since it is about noon, and it displays a lunch icon, along with other icons for common tasks. Once the lunch icon is selected, a virtual map with the closest restaurants may appear. Again, the subject may control a virtual cursor to select a lunch location. The location of icons and targets within the augmented environment may be chosen by the system in order to create more balanced training sets that sample the space more uniformly. Alternatively, they may be chosen by the system to oversample regions of control that require more refinement.

At each moment in time, the next predicted action/movement may be recorded along with the neural and EMG activity that is driving the cursor action/movement. In order to improve the accuracy of action selection and movement, control may be biased toward the predicted final actions/movements based upon where the eyes are fixated. In this way, the direction of eye gaze may be used with the neural and EMG signals to improve control. The error between the predicted action/movement based upon eye-gaze and actual action/movement creates a feedback signal to the decoder.

The recorded training data may be combined with past training data to create a larger training set for the decoder. The training data for each subset may be weighted differently, based upon performance during the collection of that dataset. The decoder that is used by the system may be derived from a combination of parameters from the new and past decoders. The parameters can be combined in a weighted fashion. In one example, greater weights are associated with decoders that are more recent. In another example, greater weights are associated with decoders that have better goodness-of-fit (less uncertainty).

Accordingly, the BCI system can be used to operate a device with high accuracy and quick error-correction even when the user intent is not explicitly provided. Such a BCI system can be used to accurately operate an augmented reality headset.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for neural or physiological interface. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure, and are intended to be within the spirit and scope of the disclosure. In other instances, an existing facility may be modified to utilize or incorporate any one or more aspects of the methods and systems described herein. Thus, in some instances, the systems may involve neural or physiological interface. Accordingly the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the following claims.

What is claimed is:

1. A method of operating a biological interface device, the method comprising:

obtaining an input signal from a subject, the input signal associated with a command for operation of the biological interface device and comprising a neural signal or a physiological signal;

processing the input signal to acquire an input set of values;

obtaining a predictive signal from the subject or an environment of the subject, the predictive signal associated with an intent for operation of the biological interface device and comprising at least one physiological predictive signal measuring physical movement of the subject;

processing the predictive signal to acquire a predictive set of values;

performing at least one calculation on the input set of values and the predictive set of values using a decoder function trained with historical data from historical input signals and historical predictive signals to produce an output set of values, the historical data including a matrix F of features and a matrix K of desired kinematic control signals for providing the output set of values, such that the matrix K is constructed by matrix multiplication of F by a matrix of regression coefficients C which represents weighted contribution of the features;

operating the biological interface device with the output set of values;

obtaining a feedback signal associated with the operation of the biological interface device and comprising a movement signal of the biological interface device;

processing the feedback signal to acquire a feedback set of values;

determining a difference between the feedback set of values and the predictive set of values; and re-training the decoder function if the difference between the feedback set of values and the predictive set of values is greater than a predetermined threshold, thereby performing co-adaptation to incorporate the feedback signal to iteratively improve the decoder function while the subject is attempting control via the biological interface device.

2. The method of claim 1, wherein the predictive signal comprises at least one of the physiological predictive signal and at least one environmental predictive signal.

3. The method of claim 2, wherein processing the predictive signal to acquire the predictive set of values comprises:

performing at least one calculation on data from the predictive signal using a predictive decoder function trained with historical data from historical predictive signals to produce the predictive set of values.

4. The method of claim 2, wherein the environmental predictive signal comprises at least one of an orientation signal, location signal, surroundings signal, temporal signal, sound signal, visual signal, verbal command, and visual command.

5. The method of claim 2, wherein the environmental predictive signal is associated with a software log of actions.

6. The method of claim 1, wherein the physiological predictive signal comprises at least one of an eye tracking signal, voice signal, movement signal, cardiac signal, skin conductance signal, and muscular signal.

7. The method of claim 1, wherein the movement signal is associated with movement of the biological interface device or movement of a cursor associated with the biological interface device.

8. The method of claim 1, further comprising presenting the movement signal to the subject in the form of at least one of visual movement of the biological interface device, visual movement of a cursor on a display of the biological interface device, visual representation of control, auditory representation of control, vibrotactile stimulation, and electrical stimulation.

9. The method of claim 1, wherein re-training the decoder function comprises obtaining a weight value associated with the feedback signal and re-training the decoder function in accordance with the weight value.

10. The method of claim 9, wherein the weight value is determined responsive to historical feedback signals.

11. The method of claim 1, further comprising presenting the predictive signal to the subject in the form of at least one of visual movement of the biological interface device, visual movement of a cursor on a display of the biological interface device, visual representation of control, auditory representation of control, vibrotactile stimulation, and electrical stimulation.

12. The method of claim 1, further comprising obtaining a training set of values from the historical input signals and the historical predictive signals.

13. The method of claim 12, further comprising updating decoder parameters with a weighted combination of data from a new training set of values and a past training set of values.

14. The method of claim 13, wherein a weight of the weighted combination is determined by at least one of uncertainty and performance of the decoder function.

15. The method of claim 1, further comprising re-training the decoder function at predetermined intervals comprising at least one of fixed intervals, adaptive intervals determined by the operation of the biological interface device, and periodic intervals determined by a user.

16. The method of claim 15, further comprising presenting a target to the subject through a visual display, augmented reality display, or virtual reality display;

obtaining the input signal from the subject, the input signal associated with a command for operation of the biological interface device in interaction with the target;

wherein re-training the decoder function comprises re-training the decoder function responsive to data from the input set of values associated with the interaction with the target.

17. The method of claim 1, wherein the predictive signal comprises an eye tracking signal and an environmental visual signal.

18. The method of claim 17, comprising operating a display device of the biological interface device with the output set of values to make a selection from a menu.

19. The method of claim 17, comprising operating a mechanical device of the biological interface device with the output set of values to actuate motion of the mechanical device.

20. The method of claim 1, wherein eye-tracking signals are utilized for estimating subject intent to be used for error-correction with the decoder function.

21. The method of claim 1, wherein the predictive signal includes an involuntary physiological signal and the input signal includes a voluntary physiological signal.

22. The method of claim 1, further comprising updating decoder parameters with a weighted combination of data from a new training set of values and a past training set of values, wherein a weight of the weighted combination is determined by uncertainty of the decoder function, such that greater weights are associated with lesser uncertainty.

23. The method of claim 22, further comprising utilizing a Gaussian filter to estimate the uncertainty of the decoder function.

24. A biological interface system comprising:

a subject signal sensor configured to collect at least one neural signal and at least one physiological signal from a subject, the at least one physiological signal measuring physical movement of the subject;

an environmental signal sensor configured to collect an environmental signal from an environment of the subject;

a signal processor operably connected to the subject signal sensor and the environmental signal sensor, the signal processor configured to generate an input set of values associated with the at least one neural signal or a first physiological signal and a predictive set of values associated with a second physiological signal or the environmental signal;

a feedback signal sensor configured to collect an actual signal from operation of the biological interface system operably connected to the signal processor, the signal processor configured to generate a feedback set of values from the actual signal;

a memory device electrically connected to the signal processor and storing data from the input set of values, and the predictive set of values, and the feedback set of values; and a system processor coupled to the memory device and configured to perform at least one calculation on the input set of values and on the predictive set of values using a decoder function trained with stored historical data to produce an output set of values, the historical data including a matrix F of features and a matrix K of desired kinematic control signals for providing the output set of values, such that the matrix K is constructed by matrix multiplication of F by a matrix of regression coefficients C which represents weighted contribution of the features, operate a biological interface device with the output set of values, and determine a difference between the feedback set of values and the predictive set of values and re-train the decoder function if the difference between the feedback set of values and the predictive set of values is greater than a predetermined threshold, thereby performing co-adaptation to incorporate the actual signal to iteratively improve the decoder function while the subject is attempting control via the biological interface device.

25. The system of claim 24, wherein the subject signal sensor comprises at least one of a microphone, a motion sensor, a temperature sensor, a light sensor, a camera, a chemical sensor, a galvanic skin response sensor, a heart rate monitor, a blood pressure monitor, an external electrode grid, an intracranial electrode grid, an intraneural electrode grid, and an intramuscular electrode grid.

26. The system of claim 24, wherein the environmental signal sensor comprises at least one of a microphone, a motion sensor, a temperature sensor, a light sensor, a camera, a chemical sensor, a global positioning system, a clock, and an orientation sensor.

27. The system of claim 24, wherein the biological interface device comprises at least one of a mechanical device and an electronic device.

28. The system of claim 24, further comprising a display device configured to display a visual indication of at least one of the neural signal, the at least one physiological signal, the environmental signal, and an actual signal associated with operation of the biological interface device.

29. The system of claim 24, further comprising a display device configured to display a target.

\* \* \* \* \*